March 22, 1966 B. O. WARREN Plant Pat. 2,615

KENTUCKY BLUEGRASS PLANT

Filed June 4, 1964

2 Sheets-Sheet 1

Inventor:
Benedict O. Warren
By: Hofgren, Wegner, Allen, Stellman & McCord
Attorneys

KENTUCKY BLUEGRASS PLANT

Filed June 4, 1964

2 Sheets-Sheet 2

Inventor:
Benedict O. Warren
By: Hofgren, Wegner, Allen, Stellman & McCord
Attorneys United States Patent Office Plant Pat. 2,615
Patented Mar. 22, 1966

2,615
KENTUCKY BLUEGRASS PLANT

Benedict O. Warren, % Warren's Turf Nursery,
8400 W. 111th St., Palos Park, Ill.

Filed June 4, 1964, Ser. No. 372,731
1 Claim. (Cl. Plt.—88)

The present invention relates to a new and distinct selection of a perennial Kentucky bluegrass plant which was discovered by me under cultivation in a fairway of a golf course near Chicago, Illinois.

After discovery of this unique plant, tillers from clumps of the plant material were placed in my greenhouse for further observation and study. Additional plants were vegetatively reproduced by me to provide sufficient plant material for more extensive observations, tests and evaluation.

After sufficient plants were vegetatively reproduced from the parent plant which I discovered, certain of the reproduced plants were studied under controlled conditions in my greenhouse, while others were placed outside in experimental plots adjacent my greenhouse for observation and study. Additional plants were also given to the Department of Agronomy of Purdue University in Lafayette, Indiana for studies by that department on a graduate level, which studies have been conducted for approximately three years.

Later, a section of the claimed Kentucky bluegrass sod was placed in an experimental plot at the Missouri Botanical Garden in St. Louis, Missouri. The experimental plot at the Missouri Botanical Garden was under the complete control, supervision and care of that organization. The test plot was made up of seventeen different experimental sod selections and three commercial bluegrass selections, which selections were laid out in block fashion adjacent each other so that, as nearly as possible, the sod selections would be subjected to the same conditions of sunlight, soil, moisture, fertilization and care. The commercial sod selections of the plot included many of the well-known commercial bluegrasses, there being a plot of Merion, a plot of a blend of Delta, Newport and Merion, and a plot of Common Kentucky.

As a result of extensive tests and observations of the claimed bluegrass plants in my greenhouse, and at Purdue University, and of the remarkable performance of this bluegrass in the test plot at the Missouri Botanical Garden, it was recognized by me that the claimed bluegrass had certain unusual properties which gave it distinct advantages for turf use over popular varieties of Kentucky bluegrass now being commercially sold such as Merion, Delta, Newport and Common Kentucky bluegrass.

From an aesthetic or appearance view point, this Kentucky bluegrass has shown an amazing ability to retain a rich deep green appearance throughout the entire growing season—spring, summer and fall. In the test plot of the Missouri Botanical Garden, this Kentucky bluegrass was the only one of the twenty sod selections tested which retained its deep rich color, and it stood out indelibly from the others, especially during the summer months (see FIGURE 1). Even in the spring and in the fall, the deep rich green color of the claimed bluegrass presented a well-recognized and observable outline in comparison to the colors of the sod selections of adjacent varieties of plants tested.

Perhaps the most distinctive physical characteristic of the claimed plant is its leaf structure. This bluegrass has leaves which are narrower and finer in texture than any other known commercial varieties of Kentucky bluegrass. In turf, the leaves generally have the texture of a red fescue and are approximately one-third as wide as Merion leaves (see FIGURE 2) and one-third to one-half as wide as Newport and Common Kentucky bluegrasses.

This Kentucky bluegrass has also exhibited outstanding regenerative properties in comparison with the well-known bluegrasses on the market. Thus, when a strip of this bluegrass sod is removed from a sod plot, the stripped portion fills in very quickly. It is believed that this unique property results from (1) the length and extensive character of the rhizomes produced by the claimed bluegrass plant, and, more particularly, (2) the depth to which the rhizomes extend beneath the surface of the ground. It is also believed that the extent and character of the rhizomes produced by the claimed bluegrass plant account in considerable measure for the plant's ability to sustain its substantially uniform appearance throughout the growing season—spring, summer and fall. New and additional crowns, and shoots from these crowns, have been observed emerging from the underlying rhizomes during the summer period of adversity when many grasses "brown out" because of weather conditions and susceptibility to bluegrass diseases. In the test plots at Purdue University, it was frequently observed that the rhizomes of this plant penetrated to unusual depths, often as much as ten inches.

The rapid regenerative capability of the claimed plant is especially important in turf areas which are subject to physical damage. Thus, on golf tees or fairways where divots are made in striking a golf ball, the ability of it to regenerate turf rapidly is an important asset.

This novel Kentucky bluegrass also exhibits strong sprouting or tillering capabilities so that isolated tillers spread outwardly much faster than do isolated tillers of Merion bluegrass. The increased spreading is accompanied by the maintenance of sufficient sprouts to provide a good density of turf.

Controlled tests and observations have also indicated a generally high level of disease resistivity of this Kentucky bluegrass as compared to other bluegrass varieties currently on the market. It has excellent resistance to Helminthosporium leaf spot, to powdery mildew, to stem rust, to stripe smut and to Helminthosporium-Curvularia,[1] which disease resistance is undoubtedly a substantial factor in providing the vigorous growth attributed to this bluegrass throughout the growing season. The vigor of this bluegrass and its dense growth suppress encroachment of undesirable plants so as to present a resilient carpet of turf.

The primary object of the present invention is to provide a bluegrass plant having the desirable properties and characteristics described above, although other objects will become apparent to those skilled in this art from the specification and claim.

The claimed Kentucky bluegrass plant is illustrated and compared with certain other varieties of Kentucky bluegrass in the accompanying color photographs, in which:

FIGURE 1 is a view of a rectangular sod plot of the claimed Kentucky bluegrass in an experimental test plot with other varieties of Kentucky bluegrass, the claimed bluegrass being the dark green sod plot and illustrating the deep green color of this Kentucky bluegrass in comparison to other bluegrass varieties nurtured under substantially the same conditions of climate, soil and fertility (the photograph being taken in August 1963);

Figure 4:
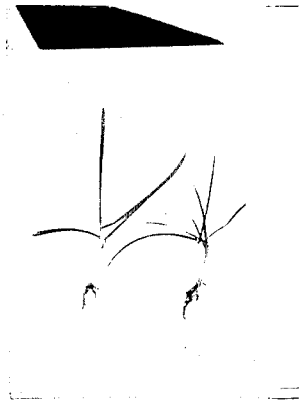
Figure 5:
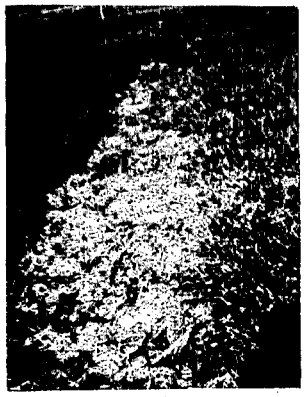
Figure 6:
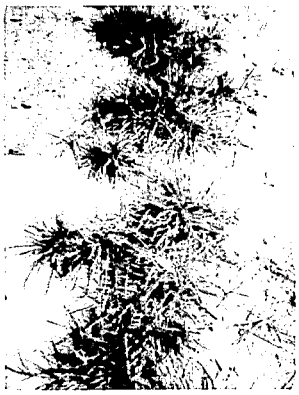
Figure 7:
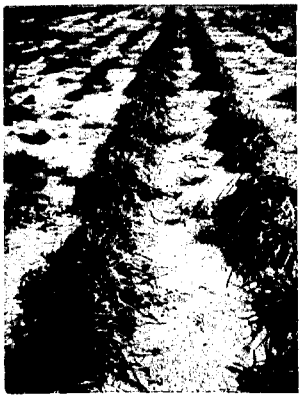
Figure 8:
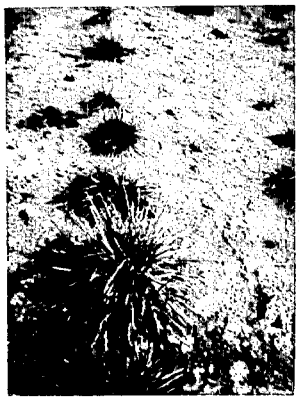

[1] The symptoms of this disease have been well characterized but the exact causal agents of this disease have not been determined.

grass being shown on the left, the leaf of the claimed Kentucky bluegrass being shown in the center, and the leaf of Common Kentucky bluegrass being shown on the right;

FIGURE 4 is a photograph showing tillers of two varieties of Kentucky bluegrass, a tiller of Merion Kentucky bluegrass being shown on the left and a tiller of the claimed Kentucky bluegrass being shown on the right;

FIGURE 5 is a photograph of a plot of the claimed Kentucky bluegrass, the photograph being taken two months after a strip of sod was taken from the plot to illustrate the regeneration of turf from rhizomes propagated by these Kentucky bluegrass plants;

FIGURE 6 is a photograph of unmowed plants of the claimed Kentucky bluegrass, the view illustrating one season's growth of individual tillers of this Kentucky bluegrass;

FIGURE 7 is a photograph illustrating unmowed Kentucky bluegrass of the claimed variety which has been vegetatively reproduced from parent plants in a field plot; and FIGURE 8 is a photograph of the progeny as produced from the seed of the claimed Kentucky bluegrass plant, the view illustrating the inability of this plant to reproduce the claimed plant with uniformity from seed.

CLASSIFICATION

This novel bluegrass exhibits those characteristics and properties which indicate that it belongs broadly in the Kentucky bluegrass classification (*Poa pratensis* L.). Although it is easily classified as this species by a number of common properties, especially the flowering stalk and the characteristics of the seed, this bluegrass is distinct from other varieties and selections of Kentucky bluegrass in a number of characteristics, for example, it has exceedingly fine narrow leaves and it is a dark green color which is maintained substantially throughout the growing season. Its seeds generally are typical of the seeds of other varieties of Kentucky bluegrass. Morphological characteristics vary slightly under the influence of varying environmental conditions.

GROWTH BEHAVIOR

The novel Kentucky bluegrass is a perennial plant. I have characterized its rate of growth as moderately rapid, which rate of growth can be made more meaningful when compared to some well-known varieties of bluegrass. As shown in FIGURE 6, single unclipped tillers of this bluegrass will often spread over an area about twelve inches across in one growing season by means of underground runners or rhizomes. The strong tillering tendencies of it permits more rapid filling of barren areas. In test results set out in Table 2, certain growth characteristics of this bluegrass were compared with those of Merion and Newport bluegrass. As seen in Table 2, this bluegrass spreads about twice as fast as either Merion or Newport bluegrass.

Unclipped mature plants of this bluegrass are generally similar in height to the Merion variety of Kentucky bluegrass, being four to six inches in height (Table 1). In comparison to Newport and Common Kentucky bluegrass growing in the same location, being of the same age and having the same cultural treatment, this bluegrass is roughly about one-half the height of Common Kentucky bluegrass and about two-thirds the height of Newport Kentucky bluegrass.

At inflorescense, the flowering stalk is one to two feet tall (Table 1), and the panicle is somewhat spreading. The appearance is typical of the Kentucky bluegrass classification. The claimed variety flowers at approximately the same time as Common Kentucky bluegrass.

As shown in Table 4, there are a significantly greater number of rhizomes developed from a single tiller of this bluegrass in comparison with either Merion or Newport bluegrass. In addition to the fact that this bluegrass develops a greater number of rhizomes, Table 5 shows that the total length of rhizomes from a single tiller of this bluegrass is also considerably greater than with Merion or Newport bluegrass; in other words, the average length of rhizomes in this plant is greater than in Merion or Newport bluegrass.

The tests and observations reported in Table 6 indicate that the average total number of shoots developed from a single tiller of this bluegrass is three times that of Merion bluegrass and over two times that of Newport bluegrass.

The claimed Kentucky bluegrass has shown itself in tests to be a hardy grass capable of adapting itself to climatical conditions in a wide area of the north central United States. Generally it has shown an ability to thrive in the more southern areas of the North Central States (where other Kentucky bluegrasses have not grown well) as well as in the cooler areas of the Northern States. It has performed well in areas with a high summer temperature and humidity such as St. Louis, Missouri; and it also has thrived in areas with severe winters, such as Chicago, Illinois, where the temperature has been as low as 20° F. below zero and ice sheets have covered the claimed bluegrass for a period of 128 days. Test plots of this bluegrass in Indiana, Missouri and Illinois have grown exceedingly well.

LEAF CHARACTERISTICS

The leaves of the novel Kentucky bluegrass are more narrow and have a finer texture than any other known variety or selection of Kentucky bluegrass. In turf, the leaves generally have the texture of a red fescue. As indicated in Table 1, its average leaf width is less than one-third that of Merion bluegrass and between one-half and one-third that of Newport and Common Kentucky bluegrass. As indicated in Table 3, the average number of new leaves per tiller is substantially the same as that of Merion and Newport bluegrass.

Figure 1:
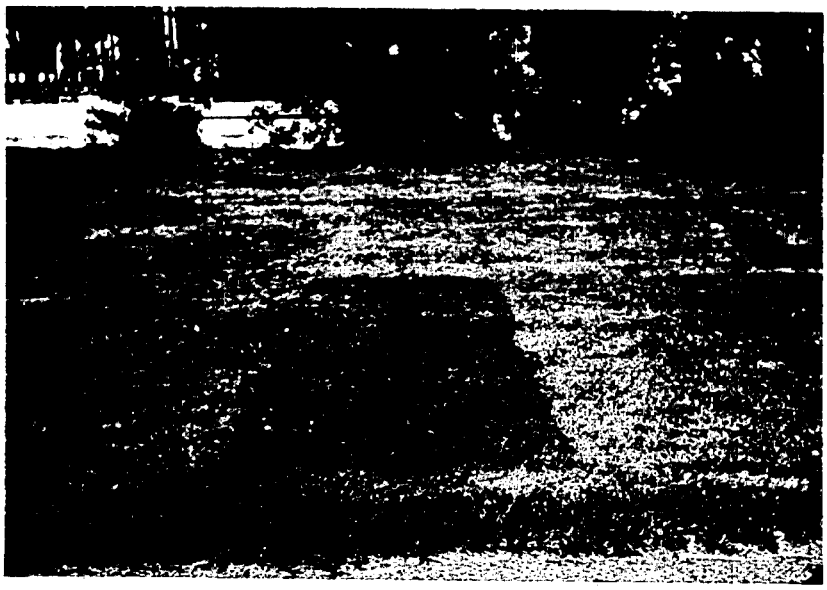
Figure 2:
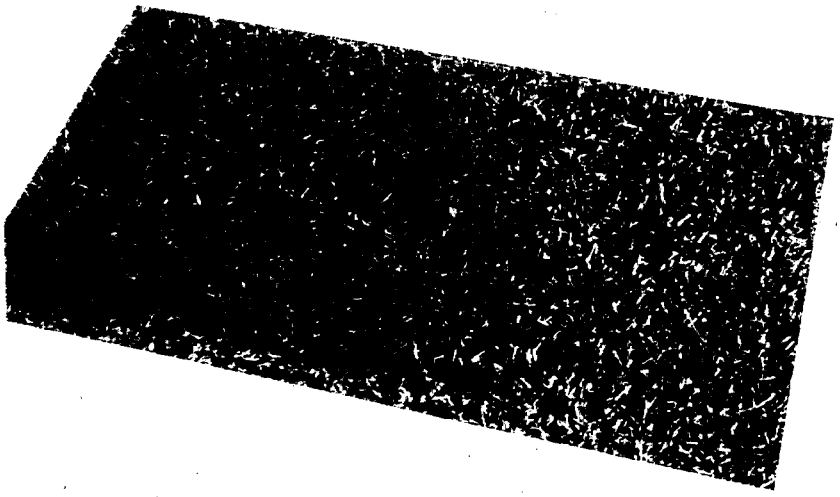
FIGURE 2 is a view of two adjacent sod selections taken at an angle of approximately 45°, and showing the fine texture of this Kentucky bluegrass on the left in comparison with the coarser texture of Merion Kentucky bluegrass on the right.
Figure 3:
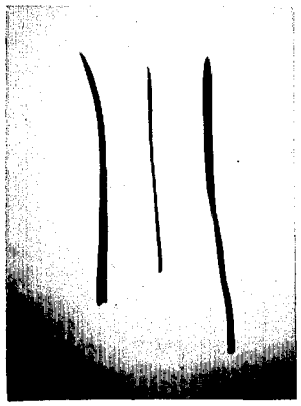
FIGURE 3 is a close-up photograph of the leaves of three Kentucky bluegrass varieties to compare their structures and textures, the leaf of Merion Kentucky blue-

In addition to their narrow structure, the leaves maintain a distinctive dark green color which is substantially unaltered throughout the growing season. A comparison of leaves of the claimed variety and Merion bluegrass leaves under similar conditions of fertility and mowing shows that the former's leaves on the Munsell color chart were 10GY 4/4, while the Merion leaves were 7BG 5/3, the comparisons being made from actual plants and not from photographs thereof. The deep distinctive color is readily seen in the plot of the novel bluegrass shown in the photograph of FIGURE 1 where the adjacent grasses are Common Kentucky (on the left) and other experimental selections (right and rear).

CYTOLOGICAL CHARACTERISTICS

Initial laboratory investigations and observations indicated that the chromosome number of the novel bluegrass is approximately 2N=48. In contrast, published literature indicates that the chromosome number for Delta bluegrass is about 71 and for Newport bluegrass is about 81.

REPRODUCTION

Reproduction of the novel bluegrass has thus far been carried out only by vegetative propogation. I have asexually reproduced the parent plant of this bluegrass a multitude of times by using rhizomes created by the parent plant, and the succeeding propagations of this bluegrass from the rhizomes have always run true in all respects to the parent plant. There has never been any sporting at any time.

I have not been able to reproduce the parent plant from seeds of the parent plant, because this bluegrass does not appear to be apomictic. The progency created by seeds of the parent plant have in observable tests been of many types and varieties, with only a few of the grasses being similar to the parent plant, for example, see the photograph, FIGURE 8.

Thus, the asexual reproduction of the novel bluegrass by vegetative propagation using rhizomes has produced uniform bluegrass plants which have been found to be genetically the same as the parent plant in growth characteristics and behavior through many successive generations of propagation.

DISEASE RESISTANCE

This Kentucky bluegrass has uniformly exhibited a generally high level of disease resistance to those common diseases to which well-known commercial types of Kentucky bluegrasses have been found to be susceptible. Eight observations at Purdue University taken from May 8, 1962, through August 20, 1962, compared this bluegrass with Merion, Newport, Delta and Common Kentucky bluegrasses (see Table 8). The novel bluegrass was found to be far superior in resistance to stripe smut and leaf rust than any of the other four grasses mentioned above. As to the diseases of the helminthosporium complex, this bluegrass was found to be significantly more resistant than Delta, Common and Newport bluegrasses, although slightly less resistant than was Merion bluegrass. However, the over-all tolerance or disease resistance of this bluegrass was observed to be better than that of any of the other four commercial bluegrasses mentioned above.

In my tests and observations at Palos Park, Illinois at my nursery, I have also observed that this bluegrass has not been damaged in test plots where a disease sometimes referred to as Helminthosporium-curvularia has severely damaged other bluegrasses such as Merion and Common Kentucky bluegrass. I have found no cases where it has been observed to be susceptible to stripe smut where commercial types of bluegrasses were attacked. I have also observed that it is extremely resistant to stem rust and shows a substantial degree of resistivity to leaf spot and powdery mildew.

*Table 1.—Comparison[1] of the claimed Kentucky bluegrass with Merion, Newport and Common Kentucky bluegrasses as to leaf width, leaf length, plant height and flower stalk height*

| | The claimed variety, mm. | Merion, mm. | Newport, mm. | Common, mm. |
|---|---|---|---|---|
| UNMOWED | | | | |
| Leaf width: | | | | |
| Average | 1.5 | 5 | 4 | 4 |
| Widest | 3.0 | 7 | 5 | 5 |
| Leaf length | 90 | 110 | 300 | 310 |
| Plant height | 110 | 120 | 170 | 200 |
| Flower stalk | 300 | 250 | 300 | 375 |
| MOWED AT 1 INCH | | | | |
| Leaf width: | | | | |
| Average | 1.0 | 2.5 | 2.5 | 3.0 |
| Widest | 1.5 | 4.0 | 5.0 | 5.0 |

[1] All comparisons between plants growing in same location, having same cultural treatment, and of the same age. Comparison tests made in summer and fall, 1963, at Palos Park, Illinois, averages being taken of twenty plants.

The observations and tests reported in Tables 2 through 6 and Table 8 were made by Charles W. Lobenstein at Purdue University, Lafayette, Indiana and are set out in his thesis submitted in partial fulfillment of requirements for the degree of doctor of philosophy, the thesis being entitled "Sod Forming Characteristics of Kentucky Bluegrass as Affected by Morphological and Physiological Factors."

*Table 2.—Comparison[1] of area of growth (expressed in square inches) of single tiller of the claimed bluegrass with single tillers of Merion and Newport bluegrasses after growing periods of 120 and 180 days, and comparison of densities of same (expressed as shoots per square inch)*

| Variety | 120 days (1962) | | 180 days (1962) | |
|---|---|---|---|---|
| | Area | Density | Area | Density |
| Claimed | 15.5 | 11.3 | 44.0 | 12.0 |
| Merion | 6.2 | 16.5 | 21.5 | 11.5 |
| Newport | 7.6 | 9.5 | 26.3 | 8.0 |

[1] All comparisons between plants growing in same location, having same cultural treatment, and of the same age.

*Table 3.—Comparison[1] of average number of new leaves per tiller in 2.5 months following May 20 and September 28, 1962*

| Variety | 5/20 to 8/4/63, number | 9/28 to 12/8/62, number |
|---|---|---|
| Claimed | 11.2 | 6.5 |
| Merion | 11.0 | 6.0 |
| Newport | 9.0 | 4.8 |

[1] All comparisons between plants growing in same location, having same cultural treatment, and of the same age.

*Table 4.—Comparison[1] of total number of rhizomes developed from single tiller of the claimed variety and two other bluegrasses*

| Variety | Growth of approximately 180 days, 5/25 to 11/15/61, clipped (1½ inch) number | Growth of approximately 60 days, 9/23/61 to 3/27/62, unclipped, number | Growth of approximately 180 days, 9/23/61 to 7/26/62, clipped (1½ inch) number |
|---|---|---|---|
| Claimed | 176 | 6.0 | 256 |
| Merion | 44 | .8 | 76 |
| Newport | 91 | 1.3 | 107 |

[1] All comparisons between plants growing in same location, having same cultural treatment, and of the same age.

*Table 5.—Comparison[1] of total length of rhizomes (expressed in meters) from single tiller (average of 8 plants)*

| Variety | Growth of approximately 180 days, 5/25 to 11/15/61, clipped (1½ inch) m. | Growth of approximately 60 days, 9/23/61 to 3/27/62, unclipped, m. | Growth of approximately 180 days, 9/23/61 to 7/26/62, clipped (1½ inch) m. |
|---|---|---|---|
| Claimed | 15.3 | .32 | 17.7 |
| Merion | 2.3 | .02 | 2.7 |
| Newport | 4.4 | .03 | 4.2 |

[1] All comparisons between plants growing in same location having same cultural treatment, and of the same age.

*Table 6.—Comparison[1] of average total number of shoots developed from a single tiller*

| Variety | Growth of approximately 180 days, 5/25 to 11/15/61, clipped (1½ inch) number | Growth of approximately 60 days, 9/23/61 to 3/27/62, unclipped, number | Growth of approximately 180 days, 9/23/61 to 7/26/62, clipped (1½ inch) number |
|---|---|---|---|
| Claimed | 823 | 47 | 517 |
| Merion | 264 | 16 | 247 |
| Newport | 388 | 14 | 198 |

[1] All comparisons between plants growing in same location, having same cultural treatment, and of the same age.

*Table 7.—Comparison [1] of disease resistance of the claimed variety and Merion Kentucky bluegrass*

| Disease | Claimed | Merion |
|---|---|---|
| Leadspot (Helminthosporium sp.) | MR | R. |
| Powdery mildew | MR | S. |
| Stem rust | R | S. |
| Stripe smut | O | S. |
| Helminthosporium-Curvularia [2] | R | S. |

[1] All comparisons between plants growing in same location, having same cultural treatment, and of the same age. The comparisons were made by visual observation on test plots at my nursery in Palos Park, Illinois during the period 1961–64, at such time as the presence of any of the above diseases were observed in any of the test plots. Similar visual observations were conducted at the St. Louis test plot during the growing season of 1963.

[2] The symptoms of this disease have been well characterized but the exact casual agents of this disease have not been determined.

M=Moderately or intermediate.
O=No disease observed where other varieties were attacked.
S=Susceptible.
R=Resistant.

What I claim and desire to be secured by Letters Patent is:

The new and distinct variety of Kentucky bluegrass, substantially as shown and described herein, characterized particularly by an attractive dark green leaf color which is substantially retained throughout the growing season, an extremely narrow leaf blade which presents a very fine texture in turf, an ability for rapid outward spreading to form a tight and dense turf, a high resistance to common grass diseases, an unusual ability to propagate deep and extensive rhizomes, and an ability to flourish in a wide area of the north central part of the United States under adverse conditions of temperature, humidity and drought.

No references cited.

ABRAHAM G. STONE, *Primary Examiner.*

*Table 8.—Comparison of foliage disease made by visual ratings at Purdue University in the summer of 1962.*[1]

| Bluegrass | Disease | 5/8 | 5/12 | 5/18 | 6/5 | 7/4 | 7/25 | 8/8 | 8/20 | Avg. Index |
|---|---|---|---|---|---|---|---|---|---|---|
| Merion | Helminthosporium sp., leaf spot, leaf blight. | 1.0 | 1.3 | 1.5 | 1.3 | 1.5 | 1.0 | 1.0 | 1.0 | 1.2 |
| | Stripe smut, unidentified leaf blight, leaf rust. | 1.3 | 2.5 | 3.0 | 2.8 | 1.0 | 1.0 | 3.2 | 9.0 | 3.0 |
| Newport | Helminthosporium sp., leaf spot, leaf blight. | 1.3 | 2.5 | 3.0 | 2.5 | 2.8 | 1.8 | 2.0 | 1.0 | 2.1 |
| | Stripe smut, unidentified leaf blight, leaf rust. | 1.0 | 3.0 | 4.5 | 4.6 | 1.0 | 1.0 | 1.0 | 1.0 | 2.1 |
| Common | Helminthosporium sp., leaf spot, leaf blight. | 2.0 | 4.3 | 5.6 | 2.6 | 2.0 | 1.3 | 1.0 | 1.0 | 2.5 |
| | Stripe smut, unidentified leaf blight, leaf rust. | ------ | 4.0 | 5.6 | 1.6 | 1.0 | 1.0 | 3.6 | 4.8 | 3.1 |
| Delta | Helminthosporium sp., leaf spot, leaf blight. | 3.0 | 5.3 | 6.6 | 3.6 | 3.3 | 1.0 | 1.6 | 1.0 | 3.2 |
| | Stripe smut, unidentified leaf blight, leaf rust. | 1.0 | 4.3 | 5.6 | 1.0 | 1.0 | 1.0 | 1.5 | 6.4 | 2.7 |
| Claimed | Helminthosporium sp., leaf spot, leaf blight. | 2.0 | 1.0 | 3.0 | 2.3 | 2.0 | 2.0 | 2.0 | 1.0 | 1.9 |
| | Stripe smut, unidentified leaf blight, leaf rust. | 1.0 | 1.0 | 2.0 | 1.0 | 1.0 | 1.0 | 1.0 | 1.3 | 1.2 |

[1] Each of the visual ratings is made on the basis of observation of four samples of each of the varieties of Kentucky bluegrass. The number (1) indicates greatest desired resistance while the number (2) indicates the worst damage or least disease resistance.